US010456556B2

(12) United States Patent
Cabiri

(10) Patent No.: US 10,456,556 B2
(45) Date of Patent: Oct. 29, 2019

(54) STEERING TOOL WITH ENHANCED FLEXIBILITY AND TRACKABILITY

(71) Applicant: Bendit Technologies Ltd., Petach Tikva (IL)

(72) Inventor: Oz Cabiri, Hod HaSharon (IL)

(73) Assignee: Bendit Technologies Ltd., Petach Tikva (IL)

( * ) Notice: Subject to any disclaimer, the term of this patent is extended or adjusted under 35 U.S.C. 154(b) by 0 days.

(21) Appl. No.: 15/898,712

(22) Filed: Feb. 19, 2018

(65) Prior Publication Data
US 2019/0255289 A1 Aug. 22, 2019

(51) Int. Cl.
*A61M 25/01* (2006.01)

(52) U.S. Cl.
CPC .... *A61M 25/0138* (2013.01); *A61M 25/0141* (2013.01); *A61M 25/0152* (2013.01); *A61M 25/0102* (2013.01)

(58) Field of Classification Search
CPC ..... A61B 1/0055; A61B 1/0057; A61B 1/307; A61B 2017/00309
See application file for complete search history.

(56) References Cited

U.S. PATENT DOCUMENTS

| 3,657,490 A * | 4/1972 | Scheiber | H04R 1/222 381/338 |
|---|---|---|---|
| 5,437,288 A * | 8/1995 | Schwartz | A61M 25/09 600/434 |
| 5,746,701 A * | 5/1998 | Noone | A61M 25/09 600/585 |
| 7,914,466 B2 * | 3/2011 | Davis | A61M 25/0013 600/585 |
| 7,914,467 B2 * | 3/2011 | Layman | A61M 25/0013 600/585 |
| 8,048,004 B2 * | 11/2011 | Davis | A61M 25/0013 600/585 |
| 8,292,827 B2 * | 10/2012 | Musbach | A61M 25/0054 600/585 |
| 8,409,114 B2 * | 4/2013 | Parins | A61M 25/00 600/585 |
| 9,750,912 B2 * | 9/2017 | McCormick | A61M 16/0488 |
| 2013/0304034 A1 * | 11/2013 | Cabiri | A61M 25/0138 604/528 |
| 2013/0304035 A1 * | 11/2013 | Cabiri | A61B 17/00234 604/528 |

(Continued)

*Primary Examiner* — Sean P Dougherty
(74) *Attorney, Agent, or Firm* — Dekel Patent Ltd.; David Klein

(57) ABSTRACT

A steering tool includes an internal tube disposed inside an external tube. The internal and external tubes are arranged for longitudinal axial movement relative to one another. A distal portion of the internal tube is fixedly joined to a distal portion of the external tube. Either or both of the tubes are formed with patterns of cuts made along adjacent longitudinal stations along a length of the cut tube. The cutting pattern at a first longitudinal station is shifted with respect to a cutting pattern at a second longitudinal station and a cutting pattern at the second longitudinal station is shifted with respect to a cutting pattern at a third longitudinal station but at a different shift defined between the first and second longitudinal stations, so that a shift from one longitudinal station of cuts to the next adjacent longitudinal station of cuts is not repeated.

13 Claims, 2 Drawing Sheets

(56) References Cited

U.S. PATENT DOCUMENTS

2015/0099997 A1* 4/2015 Cabiri .............. A61B 17/00234
  600/585
2016/0310702 A1* 10/2016 Cabiri ............... A61M 25/0136
2018/0126122 A1* 5/2018 Cabiri ................ A61B 17/1214

* cited by examiner

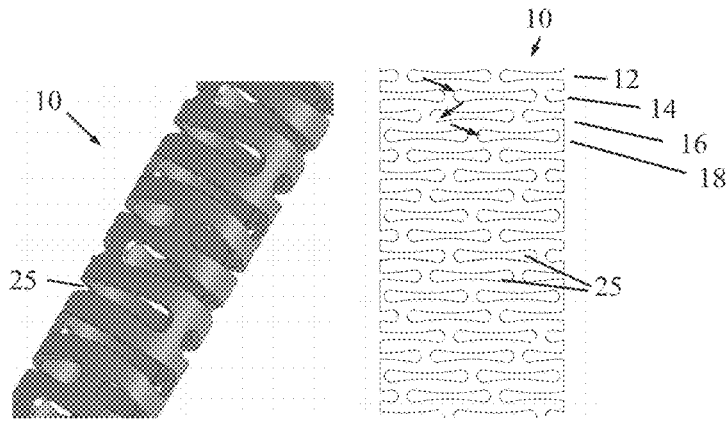
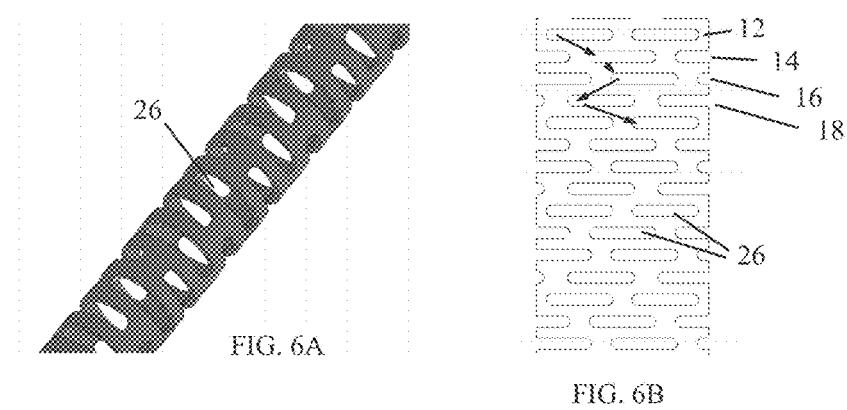
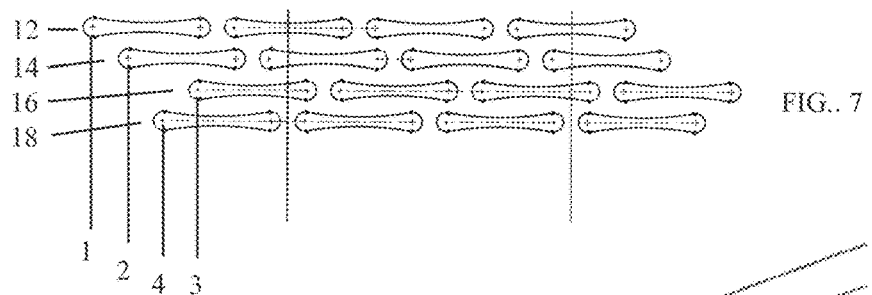
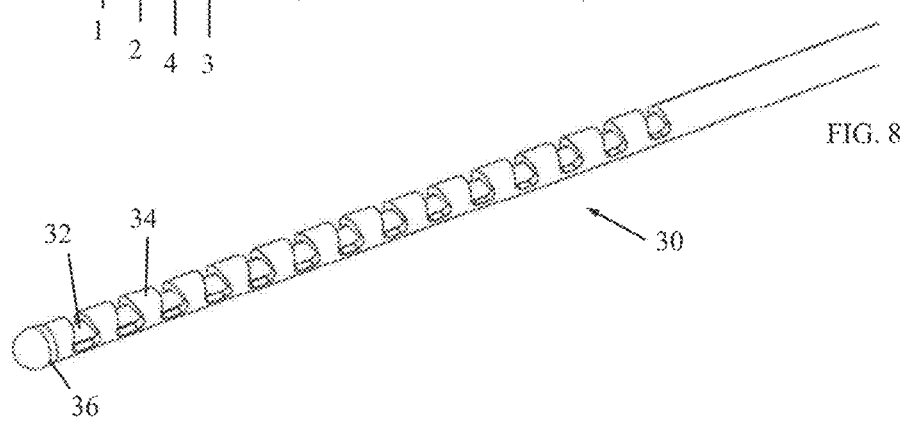

STEERING TOOL WITH ENHANCED FLEXIBILITY AND TRACKABILITY

FIELD OF THE INVENTION

The present invention generally relates to a steering tool for steering medical devices through body lumens.

BACKGROUND OF THE INVENTION

U.S. Pat. Nos. 8,684,953 and 9,138,566, to the present inventor, describe steering tools for steering medical devices through body lumens. The steering tool has an internal tube disposed inside an external tube. The internal and external tubes are arranged for longitudinal axial movement relative to one another. The distal end of the internal tube is fixedly joined to the distal end of the external tube. One or both of the internal and external tubes is slotted near the distal end thereof. The longitudinal axial movement causes bending of the distal ends of the tubes. The steering tool provides a distal tip which combines steerability, flexibility and torqueability. The tool eliminates the need for pull/push wires.

It is important for the tube to have sufficient flexibility to enable pushing the steering tool (or also called steering catheter) inside a body lumen like a blood vessel. However, it is also important that the distal end of the steering tool tracks or follows the manipulating movements of the operator at the proximal end of the tool ("trackability"). If the tool is too flexible the distal end will not respond correctly to the manipulating movements and will not properly track or follow the desired motion.

The mechanical properties of the tool material and the tool dimensions, such as but not limited to, the elasticity modulus, bending strength, shear strength, tube thickness, tube diameter, moments of inertia, and others, will determine the flexibility and trackability of the tool. Typical materials for such tubes include stainless steel alloys and nitinol, which can reduce the wall thickness, but often these tubes are too strong for bending through tortuous bends in body lumens.

Cutting the tube in a variety of shapes may improve the flexibility and trackability of the tool. However, there are disadvantages and compromises. For example, cutting the material reduces the ability to push the tube through different bends because the tube can collapse prematurely before going fully through the bend. In addition, cutting the material can increase tube elongation, create detrimental torque effects, or can create local distortions while pushing and pulling. For example, if the tube is cut so it has a shape like a spring; pushing and pulling the tube can generate rotation and unpredictable tip movements.

FIGS. 1A and 1B illustrate one prior art cutting pattern—a homogeneous spiral cutting pattern (which is one type of homogeneous spring shape). This pattern may work well with pulling, but has length changes during pushing and can generate undesirable and random rotation at the tip. Another disadvantage is that the spiral cutting transfers torque in one rotational direction (e.g., clockwise) but is limited and elongated in the opposite rotational direction (e.g., counterclockwise).

One possible solution is to connect the spiral members with stiffeners, as shown in FIGS. 2A and 2B. This is an improvement because the configuration is stiffer and less elongated in the pulling direction. However, the spiral members between the connections act like short springs. The result is this configuration still suffers from local rotations at each of the short springs; the accumulation of all the short springs can add up to a significant rotation. Another drawback is this configuration also responds differently to clockwise rotation as opposed to counterclockwise rotation.

Another possible solution is to use orthogonal connectors, as shown in FIGS. 3A and 3B and in FIGS. 4A and 4B. The connectors are perpendicular (orthogonal) to the connectors of the previous row. The cutting shape is repeated in any second row. Similar patterns may be used with greater numbers of connectors but the overall catheter stiffness would be greater.

Orthogonal cutting may be used to make a minimal number and size of connections for good flexibility. The number of cuts is limited by the tube thickness and diameter and the tube material properties. In order to achieve good tube flexibility in all directions, the cuts are shifted with respect to each other. In order to maintain a one-to-one rotational transfer from the proximal end to the distal end the cuts create identical moments of inertia all around the perimeter of the tube at any axial location on the tube.

However, the pattern consistently and continuously repeats itself in a spiral manner along the axial direction of the tube and this creates the undesirable spring effect. This is indicated by arrows 3 and 4, respectfully, in FIGS. 3A and 4A.

SUMMARY OF THE INVENTION

The present invention seeks to provide a steering tool (or catheter) with enhanced flexibility and trackability for used in body lumens, as is described more in detail hereinbelow.

The steering tool is created from a tube with patterns of cuts made along adjacent longitudinal stations along the length of the tube. The cutting pattern at the first longitudinal station is shifted with respect to the cutting pattern at the second longitudinal station. In terms of the finished cylindrical tube, "shifted" means rotationally (circumferentially) shifted. In terms of the flattened cutting pattern (if the tube were to be made from a flat pattern and then bent into a tube shape), "shifted" means linearly shifted. The cutting pattern at the second longitudinal station is shifted with respect to the cutting pattern at the third longitudinal station but at a different shift defined between the first and second longitudinal stations. In this manner, the shift from one longitudinal station of cuts to the next adjacent longitudinal station of cuts is not repeated. This breaks up the spring effect of the prior art, which is generated by monotonic repeatable shapes. An advantage is that the tube has excellent flexibility, and since the spring effect does not exist, the tube has excellent trackability and torqueability in both clockwise and counterclockwise directions.

There is thus provided in accordance with an embodiment of the present invention a steering tool including an internal tube disposed inside an external tube, the internal and external tubes being arranged for longitudinal axial movement relative to one another, wherein a distal portion of the internal tube is fixedly joined to a distal portion of the external tube at a joining zone, and the internal tube or the external tube, called a cut tube, is formed with patterns of cuts made along adjacent longitudinal stations along a length of the cut tube, and wherein a cutting pattern at a first longitudinal station is shifted with respect to a cutting pattern at a second longitudinal station and a cutting pattern at the second longitudinal station is shifted with respect to a cutting pattern at a third longitudinal station but at a different shift defined between the first and second longitudinal stations, so that a shift from one longitudinal station of cuts to the next adjacent longitudinal station of cuts is not repeated.

In accordance with an embodiment of the present invention the shift from one longitudinal station of cuts to the next adjacent longitudinal station of cuts is a circumferential shift around a perimeter of the cut tube.

In accordance with an embodiment of the present invention at least one of the cuts is elongate with straight long sides and round ends.

In accordance with an embodiment of the present invention at least one of the cuts is elongate with non-straight long sides and round ends. The non-straight long sides may be gradually narrower towards a middle portion of the at least one cut.

The steering tool has many applications in the delivery of tools or substances through body lumens, such as endovascular coiling to treat cerebral aneurysms, guiding a catheter from the aortic arch to the common carotid arteries, and from there to the carotid arterial branches to the brain and many others.

BRIEF DESCRIPTION OF THE DRAWINGS

The present invention will be understood and appreciated more fully from the following detailed description taken in conjunction with the drawings in which:

FIGS. 1A and 1B are simplified illustrations of a prior art cutting pattern (a homogeneous spiral cutting pattern) for a tube, FIG. 1A showing the flattened pattern and FIG. 1B showing the finished cylindrical tube;

FIGS. 2A and 2B are simplified illustrations of a prior art spiral cutting pattern with stiffeners, FIG. 2A showing the flattened pattern and FIG. 2B showing the finished cylindrical tube;

FIGS. 5A and 5B are simplified illustrations of a tube with a novel cutting pattern that eliminates any "spring effect", in accordance with a non-limiting embodiment of the present invention, FIG. 5A showing the finished cylindrical tube and FIG. 5B showing the flattened pattern;

FIGS. 6A and 6B are simplified illustrations of a tube with a novel cutting pattern that eliminates any "spring effect", in accordance with a non-limiting embodiment of the present invention, FIG. 6A showing the finished cylindrical tube and FIG. 6B showing the flattened pattern;

FIG. 7 is a simplified illustration of one possible cut pattern; and

FIG. 8 is a simplified illustration of a steering tool, in accordance with a non-limiting embodiment of the present invention, made with the tube of FIGS. 5A and 5B or 6A and 6B.

DETAILED DESCRIPTION OF EMBODIMENTS

Figure 1B:
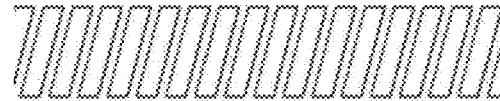
Figure 1B:
Figure 2B:
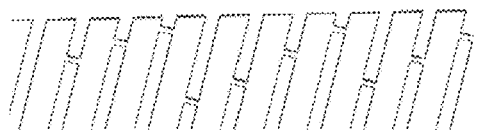
Figure 2B:
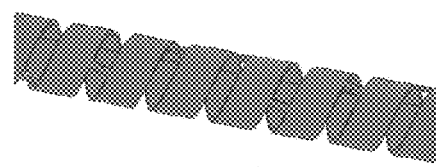
Figure 3A:
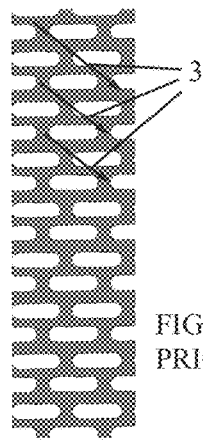
FIGS. 3A and 3B are simplified illustrations of a prior art orthogonal cutting pattern with connectors, FIG. 3A showing the flattened pattern and FIG. 3B showing the finished cylindrical tube.
Figure 3B:
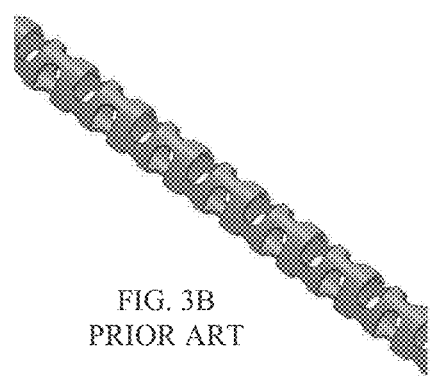
Figure 4A:
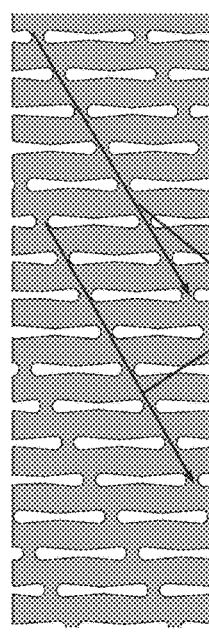
FIGS. 4A and 4B are simplified illustrations of a prior art orthogonal cutting pattern with connectors, FIG. 4A showing the flattened pattern and FIG. 4B showing the finished cylindrical tube.
Figure 4B:
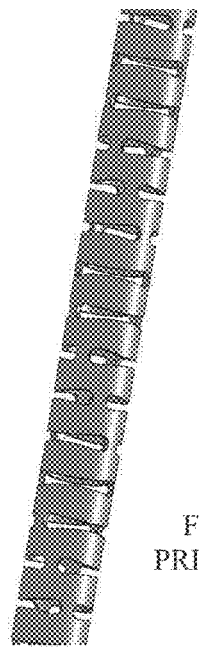

Reference is now made to FIGS. 5A and 5B, which illustrate a tube 10 which is used to make a steering tool (shown and described later with reference to FIG. 8), in accordance with a non-limiting embodiment of the present invention.

Tube 10 is formed with patterns of cuts made along adjacent longitudinal stations along the length of the tube. The cuts may be made by any suitable method, such as but not limited to, laser cutting, machining, etching and others. A cutting pattern at a first longitudinal station 12 is shifted with respect to a cutting pattern at a second longitudinal station 14. In terms of the finished cylindrical tube (FIG. 5A), "shifted" means rotationally (circumferentially) shifted. In terms of the flattened cutting pattern (FIG. 5B; if the tube were to be made from a flat pattern and then bent into a tube shape), "shifted" means linearly shifted. The cutting pattern at the second longitudinal station 14 is shifted with respect to a cutting pattern at a third longitudinal station 16 but at a different shift defined between the first and second longitudinal stations 12 and 14. The cutting pattern at the third longitudinal station 16 is shifted with respect to a cutting pattern at a fourth longitudinal station 18 but at a different shift defined between the second and third longitudinal stations 14 and 16, and so on.

In this manner, the shift from one longitudinal station of cuts to the next adjacent longitudinal station of cuts is not repeated. (This may be seen by the non-repeating arrows in FIGS. 5B and 6B.) This breaks up the spring effect of the prior art, which is generated by monotonic repeatable shapes and generates a negative spring that compensate the torque effect during elongation. "Negative spring" means any spring effect (springiness) in one direction (linear or rotational) of one row (longitudinal station) is at least partially canceled out by the spring effect of the adjacent row in another direction (linear or rotational). An advantage is that the tube has excellent flexibility, and since the spring effect does not exist, the tube has excellent trackability and torqueability in both clockwise and counterclockwise directions.

The same holds true in the embodiment of FIGS. 6A and 6B. The difference between the embodiment of FIGS. 5A/5B and that of FIGS. 6A/6B is that in the embodiment of FIGS. 6A/6B cuts 26 are elongate with straight long sides and round ends. In the embodiment of FIGS. 5A/5B cuts 25 are elongate with non-straight long sides and round ends. The non-straight long sides are gradually narrower towards the middle portion of the cut 25.

Reference is now made to FIG. 7, which illustrates one possible cut pattern in which n lateral shift locations are called 1, 2, 3, 4 . . . n. The pattern in FIG. 7 is a "1243" pattern because the cut at the first longitudinal station 12 originates from lateral location 1, the cut at the second longitudinal station 14 originates from lateral location 2, the cut at the third longitudinal station 16 originates from lateral location 4 (not 3 as in the prior art), and the cut at the fourth longitudinal station 18 originates from lateral location 3 (not 4 as in the prior art). Other possible patterns include, without limitation, 1243, 1324, 1342, 12453, 153642, 124654 and many, many others.

Reference is now made to FIG. 8, which illustrates a steering tool 30, in accordance with a non-limiting embodiment of the present invention.

Steering tool 30 includes an internal tube 32 disposed inside an external tube 34. A distal portion of internal tube 32 is fixedly joined to a distal portion of external tube 34 at a joining zone 36 ("joining" is defined below). The joining zone, for any of the embodiments, may be distanced from the distal tip of the tubes or may be at the distal tip of the tubes. The internal and external tubes 32 and 34 are arranged for longitudinal axial movement relative to one another (except for their distal portions which are joined together). Tubes 32 and 34 can additionally or alternatively rotate with respect to one another to generate a phase shift in the cuts.

The combination of those two movements causes bending and/or twisting of the distal ends of the tubes 32 and 34. One or both of the internal and external tubes 32 and 34 may be formed in accordance with the cutting patterns of FIG. 5A/5B, 6A/6B or 7.

Internal and external tubes 32 and 34 may be made of any suitably flexible, medically safe material, such as but not limited to, stainless steel (e.g., AISI 316), nitinol, cobalt-chromium alloy, nickel-titanium alloy, and others, glass fibers, plastics (e.g., nylon, polypropylene, PEBAX and many others) or combinations thereof.

The term "joining" encompasses any method for attaching the materials of the tubes together, such as but not limited to, welding, ultrasonic welding, thermal bonding, adhesive bonding, molding, and others.

What is claimed is:

1. A steering tool comprising:
an internal tube disposed inside an external tube, said internal and external tubes being arranged for longitudinal axial movement relative to one another, wherein a distal portion of said internal tube is fixedly joined to a distal portion of said external tube at a joining zone, and
said internal tube or said external tube is formed with patterns of cuts made along adjacent longitudinal stations along a length thereof, and wherein a cutting pattern at a first longitudinal station is shifted with respect to a cutting pattern at a second longitudinal station and a cutting pattern at the second longitudinal station is shifted with respect to a cutting pattern at a third longitudinal station but at a different shift defined between said first and second longitudinal stations, so that a shift from one longitudinal station of cuts to the next adjacent longitudinal station of cuts is not repeated, and wherein at each of said longitudinal stations said cuts are separated from each other by a separation and centers of the separations of said first, second and third longitudinal stations, when said internal tube or said external tube is in an unfolded position as a flat type sheet, do not lie on a common straight axis, wherein said common straight axis touches and is centered on each of the separations.

2. The steering tool according to claim 1, wherein the shift from one longitudinal station of cuts to the next adjacent longitudinal station of cuts is a circumferential shift around a perimeter of said internal tube or said external tube.

3. The steering tool according to claim 1, wherein at least one of said cuts is elongate with straight long sides and round ends.

4. The steering tool according to claim 1, wherein at least one of said cuts is elongate with non-straight long sides and round ends.

5. The steering tool according to claim 4, wherein said non-straight long sides are gradually narrower towards a middle portion of said at least one cut.

6. The steering tool according to claim 1, wherein springiness in one direction of one of said longitudinal stations is at least partially canceled out by springiness of an adjacent one of said longitudinal stations in another direction.

7. The steering tool according to claim 1, wherein shifting of said patterns of cuts comprises n lateral shift locations, called 1, 2, 3, 4 . . . n.

8. The steering tool according to claim 7, wherein the shifting comprises a pattern of 1243 lateral shift locations.

9. The steering tool according to claim 7, wherein the shifting comprises a pattern of 1324 lateral shift locations.

10. The steering tool according to claim 7, wherein the shifting comprises a pattern of 1342 lateral shift locations.

11. The steering tool according to claim 7, wherein the shifting comprises a pattern of 12453 lateral shift locations.

12. The steering tool according to claim 7, wherein the shifting comprises a pattern of 153642 lateral shift locations.

13. The steering tool according to claim 7, wherein the shifting comprises a pattern of 124654 lateral shift locations.

* * * * *